United States Patent
Chen et al.

(10) Patent No.: US 8,236,341 B2
(45) Date of Patent: Aug. 7, 2012

(54) POLY(TETRAFLUOROETHYLENE) POLYMER WITH NITRIC OXIDE DONATING SURFACE

(75) Inventors: Mingfei Chen, Santa Rosa, CA (US); Ayala Hezi-Yamit, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 604 days.

(21) Appl. No.: 12/417,335

(22) Filed: Apr. 2, 2009

(65) Prior Publication Data

US 2010/0256755 A1    Oct. 7, 2010

(51) Int. Cl.
| | |
|---|---|
| C08F 8/30 | (2006.01) |
| C08F 14/18 | (2006.01) |
| C09D 127/22 | (2006.01) |
| A61L 27/34 | (2006.01) |
| A61L 31/10 | (2006.01) |
| C08K 5/22 | (2006.01) |

(52) U.S. Cl. ........ 424/423; 424/422; 424/425; 424/426; 623/11.11

(58) Field of Classification Search .................. 424/422, 424/423, 425, 426; 623/11.11
See application file for complete search history.

(56) References Cited

U.S. PATENT DOCUMENTS

| | | | |
|---|---|---|---|
| 5,362,718 A | 11/1994 | Skotnicki et al. | |
| 6,015,815 A | 1/2000 | Mollison | |
| 6,329,386 B1 | 12/2001 | Mollison | |
| 7,201,935 B1 | 4/2007 | Claude et al. | |
| 2006/0134165 A1* | 6/2006 | Pacetti | 424/422 |
| 2007/0264225 A1 | 11/2007 | Cheng et al. | |

FOREIGN PATENT DOCUMENTS

| | | |
|---|---|---|
| WO | WO 2009/014829 | 1/2009 |
| WO | WO 2009/117182 | 9/2009 |
| WO | WO 2009/117183 | 9/2009 |

* cited by examiner

*Primary Examiner* — Ana Woodward

(57) ABSTRACT

Described herein are nitric oxide (NO)-donating poly(tetrafluoroethylene) (PTFE) polymers and polymer surfaces and methods of making and using the same. The NO-donating PTFE polymers can be used to fabricate at least a portion of an implantable medical device, coat at least a portion of an implantable medical device or form at least a portion of an implantable medical device. The NO-donating PTFE polymers provide controlled release of NO once implanted at or within the target site.

15 Claims, No Drawings

POLY(TETRAFLUOROETHYLENE) POLYMER WITH NITRIC OXIDE DONATING SURFACE

FIELD OF THE INVENTION

Described herein are nitric oxide (NO)-donating poly(tetrafluoroethene) (PTFE) polymers for medical devices.

BACKGROUND

Medical research is rapidly discovering therapeutic applications for nitric oxide (NO), a simple diatomic signaling molecule, including fields of vascular surgery and interventional cardiology. It has been known for some time now that NO is a signaling molecule with properties such as anti-inflammation, anti-restenosis, vasodilatation and promotion of endothelization. Recently, however, NO has been shown to significantly reduce thrombocyte aggregation and adhesion. Thrombocyte aggregation occurs within minutes following the initial vascular insult and once the cascade of events leading to restenosis is initiated, irreparable damage can result. Moreover, the risk of thrombogenesis and restenosis persists until the endothelium lining the vessel lumen has been repaired. Therefore, it is essential that NO, or any anti-restenotic agent, reach the injury site immediately.

One approach for providing a therapeutic level of NO at an injury site is to increase systemic NO levels prophylactically. This can be accomplished by stimulating endogenous NO production or using exogenous NO sources. Exogenous NO sources such as pure NO gas are highly toxic, short-lived and relatively insoluble in physiological fluids. Consequently, systemic exogenous NO delivery is generally accomplished using organic nitrate prodrugs such as nitroglycerin tablets, intravenous suspensions, sprays and transdermal patches. The human body rapidly converts nitroglycerin into NO; however, enzyme levels and co-factors required to activate the prodrug are rapidly depleted, resulting in drug tolerance. Moreover, systemic NO administration can have devastating side effects including hypotension and free radical cell damage. Therefore, using organic nitrate prodrugs to maintain systemic anti-restenotic therapeutic blood levels is not currently possible.

Therefore, considerable attention has been focused on localized, or site specific, NO delivery to ameliorate the disadvantages associated with systemic prophylaxis. Implantable medical devices coated with NO-releasing compounds have been evaluated. Implantable medical device coatings or substances used as medical devices need to be biocompatible yet function as a reservoir for the bioactive agent and sustain an appropriate controlled release of the bioactive agent.

Poly(tetrafluoroethylene) (PTFE) is widely used in implantable medical devices, in conjunction with a medical device or as a device itself. PTFE as an implantable material generally shows biocompatibility. However, as with any implantable material, there are continued efforts to improve the biocompatibility of PTFE through surface engineering. One common surface engineering procedure involves the introduction of poly(ethylene glycol) groups on the surface. This procedure adds hydrophilicity to the material, thereby increasing its biocompatibility.

Consequently, an implantable material such as PTFE with an engineered surface with increased biocompatibility coupled with the local delivery of NO may prove to be beneficial. The present disclosure attempts to fulfill this shortcoming by providing modified PTFE surfaces which can bind and controllably release NO to the surrounding tissues.

SUMMARY

Described herein are NO-donating poly(tetrafluoroethylene) (PTFE) polymers and polymer surfaces and methods of making and using the same. The NO-donating PTFE polymers can be used in implantable medical devices, to form implantable medical devices or to fabricate at least a portion of an implantable medical device. The NO-donating PTFE polymers provide controlled release of NO once implanted at or within the target site.

In one embodiment described herein are nitric oxide (NO)-donating polymers comprising: a poly(tetrafluoroethylene) polymer having the structure:

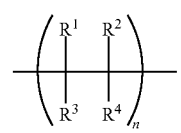

(Formula 1)

wherein n is an integer between 1 and 25,000 and wherein each of $R^1$-$R^4$ is independently fluorine or a tertiary amine having the structure:

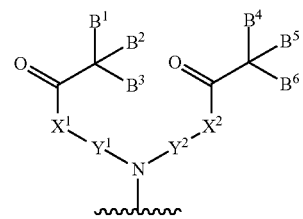

(Formula 2)

wherein $X^1$ and $X^2$ are each independently O or not present, $Y^1$ and $Y^2$ are each independently selected from $C_1$ to $C_{10}$ alkyl, $C_1$ to $C_{10}$ alkenyl, $C_1$ to $C_{10}$ alkynyl, $C_3$ to $C_8$ cyclic alkyl, or any combination thereof, and each of $B^1$-$B^6$ is independently hydrogen or a diazeniumdiolate (DD) group, with the proviso that at least one of $B^1$-$B^6$ is a DD group; wherein at least one of $B^1$-$B^6$ is a tertiary amine of the structure of Formula 2. In another embodiment, $Y^1$ and $Y^2$ are —$CH_2$—.

In other embodiments, the polymer is associated with an implantable medical device, the medical device being selected from stents, catheters, micro-particles, probes, vascular grafts, and combinations thereof.

Further described herein are implantable medical devices comprising an NO-donating polytetrafluoroethylene polymer having a polymeric surface comprising the structure:

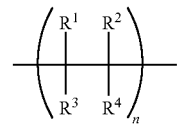

wherein n is an integer between 1 and 25,000 and wherein each of $R^1$-$R^4$ is independently fluorine or a tertiary amine having the structure:

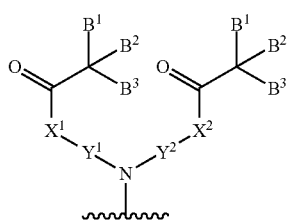

(Formula 2)

wherein $X^1$ and $X^2$ are each independently O or not present, $Y^1$ and $Y^2$ are each independently selected from $C_1$ to $C_{10}$ alkyl, $C_1$ to $C_{10}$ alkenyl, $C_1$ to $C_{10}$ alkynyl, $C_3$ to $C_8$ cyclic alkyl, or any combination thereof, and each of $B^1$-$B^6$ is independently hydrogen or a diazeniumdiolate (DD) group, with the proviso that at least one of $B^1$-$B^6$ is a DD group;

wherein at least one of $R^1$-$R^4$ is a tertiary amine of the structure of Formula 2.

In another embodiment, the medical device is selected from stents, catheters, micro-particles, probes, vascular grafts, and combinations thereof. In yet another embodiment, the medical device further comprises a parlyene primer layer and/or a cap coat. In still further embodiments, the polymer comprises one or more bioactive agents selected from anti-proliferatives, estrogens, chaperone inhibitors, protease inhibitors, protein-tyrosine kinase inhibitors, leptomycin B, peroxisome proliferator-activated receptor gamma ligands (PPARγ), hypothemycin, bisphosphonates, epidermal growth factor inhibitors, antibodies, proteasome inhibitors, antibiotics, anti-inflammatories, anti-sense nucleotides and transforming nucleic acids, cytostatic compounds, toxic compounds, chemotherapeutic agents, analgesics, antibiotics, protease inhibitors, statins, nucleic acids, polypeptides, growth factors and delivery vectors, liposomes, and combinations thereof.

Further still, described herein is a method of making a NO releasing PTFE polymer comprising the steps of: providing a PTFE polymer; plasma treating the PTFE polymer with ammonia thereby forming an amino functionalized PTFE polymer; treating the amino functionalized polymer with an acetyl functionalized compound thereby forming an acetyl functionalized PTFE polymer; and subjecting the acetyl functionalized PTFE polymer to NO thereby forming a diazeniumdiolated PTFE polymer. In one embodiment, the plasma treatment is at an energy of about 20 W.

In another embodiment, the one or more acetyl functionalized compounds is ethyl acetate or methyl acetate. Further, the diazeniumdiolated PTFE polymer has the structure:

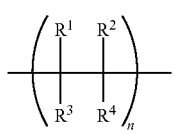

(Formula 1)

wherein n is an integer between 1 and 25,000 and wherein each of $R^1$-$R^4$ is independently fluorine or a tertiary amine having the structure:

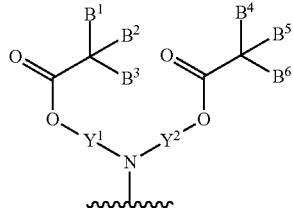

Formula 5 wherein $Y^1$ and $Y^2$ are each independently selected from $C_1$ to $C_{10}$ alkyl, $C_1$ to $C_{10}$ alkenyl, $C_1$ to $C_{10}$ alkynyl, $C_3$ to $C_8$ cyclic alkyl, or any combination thereof, and each of $B^1$-$B^6$ is independently hydrogen or a diazeniumdiolate (DD) group, with the proviso that at least one of $B^1$-$B^6$ is a DD group; wherein at least one of $R^1$-$R^4$ is a tertiary amine of the structure of Formula 5.

In another embodiment, the method further comprises the step of coating the PTFE polymer on a medical device or forming a medical device out of the PTFE polymer.

In still a further embodiment, described herein is an NO-donating vascular stent comprising: a stent; and an NO-donating polytetrafluoroethylene polymer coating disposed upon the stent wherein the polymer has the structure:

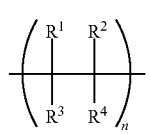

(Formula 1)

wherein n is an integer between 1 and 25,000 and wherein each of $R^1$-$R^4$ is independently fluorine or a tertiary amine having the structure:

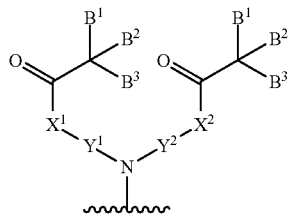

(Formula 2)

wherein $X^1$ and $X^2$ are each independently O or not present, $Y^1$ and $Y^2$ are each independently selected from $C_1$ to $C_{10}$ alkyl, $C_1$ to $C_{10}$ alkenyl, $C_1$ to $C_{10}$ alkynyl, $C_3$ to $C_8$ cyclic alkyl, or any combination thereof, and each of $B^1$-$B^6$ is independently hydrogen or a diazeniumdiolate (DD) group, with the proviso that at least one of $B^1$-$B^6$ is a DD group; wherein at least one of $R^1$-$R^4$ is a tertiary amine of the structure of Formula 2.

Definition of Terms

The following definition of terms is provided as a helpful reference for the reader. The terms used in this patent have specific meanings as they related to the present invention. Every effort has been made to use terms according to their ordinary and common meaning. However, where a discrepancy exists between the common ordinary meaning and the following definitions, these definitions supersede common usage.

Bioactive Agent(s): As used herein, "bioactive agent" shall include any compound or drug having a therapeutic effect in an animal. Exemplary, non limiting examples include anti-proliferatives including, but not limited to, macrolide antibiotics including FKBP-12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. Drugs can also refer to bioactive agents including anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, liposomes, and the like.

Exemplary FKBP-12 binding agents include sirolimus (rapamycin), tacrolimus (FK506), everolimus (certican or RAD-001), temsirolimus (CCI-779 or amorphous rapamycin 42-ester with 3-hydroxy-2-(hydroxymethyl)-2-methylpropionic acid as disclosed in U.S. patent Ser. No. 10/930,487) and zotarolimus (ABT-578; see U.S. Pat. Nos. 6,015,815 and 6,329,386). Additionally, other rapamycin hydroxyesters as disclosed in U.S. Pat. No. 5,362,718 may be used in combination with the polymers of the present invention.

Compatible: As used herein, "compatible" refers to a composition possessing the optimum, or near optimum combination of physical, chemical, biological and drug release kinetic properties suitable for a controlled-release coating made in accordance with the teachings of the present disclosure. Physical characteristics include durability and elasticity/ductility, chemical characteristics include solubility and/or miscibility and biological characteristics include biocompatibility. The drug release kinetic should be either near zero-order or a combination of first and zero-order kinetics.

Controlled release: As used herein "controlled release" refers to the release of a bioactive compound from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments an initial burst of drug may be desirable followed by a more gradual release thereafter. The release rate may be steady state (commonly referred to as "timed release" or zero order kinetics), that is the drug is released in even amounts over a predetermined time (with or without an initial burst phase) or may be a gradient release. A gradient release implies that the concentration of drug released from the device surface changes over time.

Copolymer: As used herein, a "copolymer" will be defined as a macromolecule produced by the simultaneous chain addition polymerization of two or more dissimilar units such as monomers. Copolymer shall include bipolymers (two dissimilar units), terpolymers (three dissimilar units), etc.

Glass Transition Temperature ($T_g$): As used herein "glass transition temperature" or $T_g$ refers to a temperature wherein a polymer structurally transitions from a elastic pliable state to a rigid and brittle state.

$M_n$: As used herein, $M_n$ refers to number-average molecular weight. Mathematically it is represented by the following formula:

$$M_n = \Sigma_i N_i M_i / \Sigma_i N_i,$$

wherein the $N_i$ is the number of moles whose weight is $M_i$.

$M_w$: As used herein, $M_w$ refers to weight average molecular weight that is the average weight that a given polymer may have. Mathematically it is represented by the following formula:

$$M_w = \Sigma_i N_i M_i^2 / \Sigma_i N_i M_i,$$

wherein $N_i$ is the number of molecules whose weight is $M_i$.

DETAILED DESCRIPTION

Described herein are NO-donating poly(tetrafluoroethylene) (PTFE) polymers and polymer surfaces and methods of making and using the same. The NO-donating PTFE polymers can be used to fabricate at least a portion of an implantable medical device, coat at least a portion of an implantable medical device or form at least a portion of an implantable medical device. The NO-donating PTFE polymers provide controlled release of NO once implanted at or within the target site.

A NO-donating PTFE polymer according to the present description has a structure

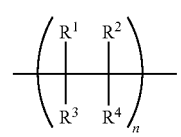

Formula 1 wherein n is an integer between 1 and 25,000 and wherein each of $R^1$-$R^4$ is independently fluorine or a tertiary amine having the structure

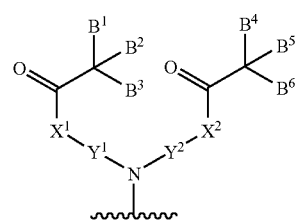

Formula 2 wherein $X^1$ and $X^2$ are each independently O or not present, $Y^1$ and $Y^2$ are each independently selected from $C_1$ to $C_{10}$ alkyl, $C_1$ to $C_{10}$ alkenyl, $C_1$ to $C_{10}$ alkynyl, $C_3$ to $C_8$ cyclic alkyl, or any combination thereof, and each of $B^1$-$B^6$ is independently hydrogen or a diazeniumdiolate (DD) group, with the proviso that at least one of $B^1$-$B^6$ is a DD group. The acetyl group can be attached to $Y^1$ or $Y^2$ at any position thereon.

A DD group is a complex capable of releasing NO once implanted at a target site in situ. One or more DD group is bound to an α-carbon adjacent to a carbonyl group and have the general structure.

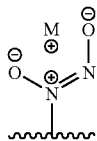

Formula 3 wherein M is a metal or other cationic molecule with the appropriate charge to stabilize the DD group. In one embodiment, the charge on M matches the valence of the DD group. Depending on the number of hydrogen on the α-carbon adjacent to a carbonyl group, at least one, but as many as three of the hydrogen can be replaced by a DD group. If all three hydrogen are replaced, the general structure will be:

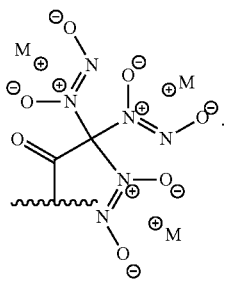

Formula 4

Generally, n can be an integer between about 1 and about 5,000, or about 1 and about 1,000, or about 1 and about 500, or about 1 and about 100.

The NO-donating PTFE polymers can be used to form at least a portion of an implantable medical device. For example, the NO-donating PTFE polymers can be used to form a sleeve or a pouch for an implantable medical device such as a stent graft. A stent graft, as described herein, is composed of a NO-donating PTFE polymer supported by a rigid structure such as metal scaffolding.

The NO-donating PTFE polymers can also be formed into a medical device with structural support such as a stent itself, or a portion thereof. The PTFE material can be extruded or formed into an appropriate shape. Specific shapes can be extruded such as, but not limited to, boxes, cylinders, rods, fibers or sheets. Additionally, PTFE material can be stretched into shapes such as fibers. Fibers, for example, can be woven into polymeric "fabrics" similar to polyester equivalents. These fabrics can be useful in many aspects of implantable medical device manufacturing, including grafting material.

The NO-donating PTFE polymers described herein are used to coat medical devices deployed in a hemodynamic environment. As such, the NO-donating PTFE polymers possess excellent adhesive properties. That is, the coating has the ability to be stably coated on the medical device surface.

The medical devices used may be permanent medical implants, temporary implants, or removable devices. For example, and not intended as a limitation, the medical devices may include stents, catheters, micro-particles, probes, and vascular grafts (also known as stent graft).

In one embodiment, the medical device is a stent or stents. The stents may be vascular stents, urethral stents, biliary stents, or stents intended for use in other ducts and organ lumens. Vascular stents, for example, may be used in peripheral, cerebral, or coronary applications. The stents may be rigid expandable stents or pliable self-expanding stents. Many different materials can be used to fabricate the implantable medical devices including, but not limited to, stainless steel, nitinol, aluminum, chromium, titanium, gold, cobalt, ceramics, and a wide range of synthetic polymeric and natural materials including, but not limited to, collagen, fibrin and plant fibers. All of these materials, and others, may be used with the polymeric coatings made in accordance with the teachings disclosed herein. Furthermore, the polymers described herein can be used to fabricate an entire medical device.

Vascular stents are implanted into coronary arteries immediately following angioplasty. In another embodiment, vascular stents are implanted into the abdominal aorta to treat an abdominal aneurysm.

There are many theories that attempt to explain, or contribute to our understanding of how polymers adhere to surfaces. The most important forces include electrostatic and hydrogen bonding. However, other factors including wettability, absorption and resiliency also determine how well a polymer will adhere to different surfaces. Therefore, polymer base coats, or primers are often used in order to create a more uniform coating surface.

The NO-donating PTFE polymers described herein can be applied to medical device surfaces, either primed or bare, in any manner known to those skilled in the art. Commonly, PTFE is a solid or white powder at room temperature and pressure. Application methods for the NO-donating PTFE polymers include, but are not limited to, spraying, dipping, brushing, vacuum-deposition, and others. As such, it is not uncommon for the solid PTFE to be heated to temperatures exceeding 500° C. thereby creating a molten PTFE. The molten PTFE can then be used to subsequently coat an implantable medical device using any means known in the art.

The NO-donating PTFE polymer can be modified, pretreated or functionalized before coating onto a medical device or thereafter to allow one or more additional coatings to properly "stick" or bond to the NO-donating PTFE polymer or medical device. Suited pre-treatment methods can be found in the vacuum deposition or irradiation technologies; moreover, wet chemical modification of PTFE has been described comprising reduction of the carbon-fluorine bonds with the purpose of modifying its adhesive and wetting surface properties, as well as allowing subsequent surface modification reactions to take place.

One or more additional polymer coatings may be applied to the medical device in any position relative to the medical device surface. In one embodiment, the NO-donating PTFE polymer layer is applied over a primer layer. In another embodiment, the additional layer may be between the primer layer and the NO-donating PTFE polymer layer or may be between the NO-donating PTFE polymer layer and the cap coat. Further, the additional layer may be on top of the cap coat.

The NO-donating PTFE polymers may optionally be used with a cap coat. A cap coat as used herein refers to the outermost coating layer applied over another coating. A NO-donating PTFE polymer is applied over a bare medical device surface or a primer coat on the surface of the medical device. Then, a polymer cap coat can be applied over the NO-donating PTFE polymeric coating. The cap coat may optionally serve as a diffusion barrier to control the NO release. The cap coat may be merely a biocompatible polymer applied to the surface of the sent to protect the stent and have no effect on the NO release rates.

The polymer chosen for a primer layer or as a cap coat is preferably a polymer that is biocompatible and minimizes irritation to the vessel wall when the medical device is implanted. The polymer may be either a biostable or a bioabsorbable polymer depending on the desired rate, when used as a cap coat, of release or the desired degree of polymer stability. Bioabsorbable polymers that can be used include poly(L-lactic acid), polycaprolactone, poly(lactide-co-glycolide), poly(ethylene-vinyl acetate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid.

Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, ethylene-co-vinylacetate, polybutylmethacrylate, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

In an exemplary embodiment, the primer coat is parlyene applied to a metal stent. Parylene can provide scaffolding on the medical device for other polymers or polymer systems. In such an embodiment, the NO-donating PTFE polymers can be directly applied to the primer layer or to one or more layers applied to the primer layer.

The additional coating may further comprise one or more additional bioactive agents. The bioactive agent may further be incorporated into the NO-donating PTFE polymer layer. The choice of bioactive agent to incorporate, or how much to incorporate, will have a great deal to do with the polymer selected to coat or form the implantable medical device. A person skilled in the art will appreciate that hydrophobic agents prefer hydrophobic polymers and hydrophilic agents prefer hydrophilic polymers. Therefore, coatings and medical devices can be designed for agent or agent combinations with immediate release, sustained release or a combination of the two.

Exemplary, non limiting examples of bioactive agents that can be incorporated into the NO-donating PTFE polymer described herein include anti-proliferatives including, but not limited to, macrolide antibiotics including FKBP-12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. Drugs can also refer to bioactive agents including anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, liposomes, and the like.

Exemplary FKBP-12 binding agents include sirolimus (rapamycin), tacrolimus (FK506), everolimus (certican or RAD-001), temsirolimus (CCI-779 or amorphous rapamycin 42-ester with 3-hydroxy-2-(hydroxymethyl)-2-methylpropionic acid as disclosed in U.S. patent Ser. No. 10/930,487) and zotarolimus (ABT-578; see U.S. Pat. Nos. 6,015,815 and 6,329,386). Additionally, other rapamycin hydroxyesters as disclosed in U.S. Pat. No. 5,362,718 may be used in combination with the polymers described herein.

Although it is within the scope of the present disclosure that additional bioactive agents can be useful in treating a plethora of medical conditions, in some exemplary embodiments, the use of a NO-donating PTFE polymer can alleviate the need for additional bioactive agents. The NO-donating PTFE polymers described herein have the effect of providing cardiovascular effects such as, but not limited to, vasodilatation, anti-inflammation and anti-restenosis. Therefore, medical devices incorporating these polymers or polymeric systems can have the benefit of alleviating the need for supplemental bioactive agents to treat vasoconstriction, inflammation and restenosis. Removing such bioactive agents from a patient's post implantation treatment can help reduce side effects associated with the systemic, or even local, administration of such agents.

Additionally, removing such agents from systemic administration or local delivery from the same medical device can reduce the complexity of the treatment. For example, some bioactive agents may not work well together or may require separate polymer systems in order to achieve controlled release from the implanted device.

Further described herein are methods of forming NO-donating PTFE polymers. Initially, the method begins by providing a PTFE polymer. As one skilled in the art is aware, PTFE is highly hydrophobic as a result of its symmetrically arranged fluorine. It is this symmetrical arrangement of the fluorine that gives PTFE "non-sticky," robust properties, which make Teflon® (Du Pont, Wilmington, Del.) such a popular product. This properly aids in the PTFE polymer's biocompatibility.

A PTFE polymer has the general structure:

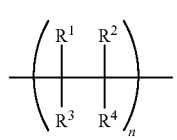

Formula 1 wherein n is an integer between 1 and 25,000 and wherein each of $R^1$-$R^4$ is independently fluorine or a tertiary amine. On skilled in the art will understand that by varying one or more of the fluorine to a more hydrophilic constituent, the polymer will attain a more hydrophilic properties and may be more useful depending on the application. Additionally, varying n will change the physical properties of the PTFE polymer. A smaller n will result in a less rigid polymer with a lower melting point and $T_g$. A larger n will result in a more rigid polymer with a higher melting point and $T_g$.

In order to form the NO-donating PTFE polymers described herein, the PTFE polymer must first be plasma treated. Plasma treatment can occur in the presence of a gas selected from the group consisting of hydrogen, nitrogen, ammonia, oxygen, carbon dioxide, $C_2F_6$, $C_2F_4$, $C_3F_6$, $C_2H_4C_2H_2$, $CH_4$, and mixtures thereof. The plasma may be generated using microwave, DC, inductive ratio frequency power source, or combinations thereof. The energy used for plasma is generally in the range of about 10 W to about 50 W, preferably about 20 W. Plasma treatment can be used to functionalize a surface for subsequent chemical reaction or modification of the substantially un-reactive PTFE polymer. In one embodiment, the PTFE polymer is plasma treated with ammonia gas to create an amino functionalized PTFE polymer as depicted below in Reaction 1.

Reaction 1

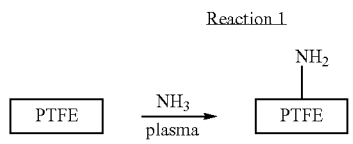

Once an amino functionalized PTFE polymer has been created, the functionalized amino groups can be substituted with virtually any compound capable of reacting with an amino group. Preferably, a halogenated compound is reacted with the functionalized amino group. Compounds useful in creating DD-loadable scaffolding include $C_1$ to $C_{10}$ alkyl, $C_1$ to $C_{10}$ alkenyl, $C_1$ to $C_{10}$ alkynyl, $C_3$ to $C_8$ cyclic alkyl, or any combination thereof. Any of the above compounds can be substituted with a halogen in order to more easily attain a reaction with the amino group. Regardless of the scaffolding chosen, the scaffolding includes at least one acetyl group or the ability to accept an acetyl group through further substitution.

Further, since the amino functionalized PTFE polymer includes primary amines on its surface, the primary amines can be substituted twice at each amino group. Once the amino functionalized PTFE polymer is substituted with at least one acetyl containing compound, an acetyl functionalized PTFE polymer is formed. Such an acetyl functionalized PTFE polymer is illustrated below in Formula 5.

Formula 5

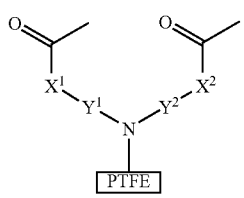

wherein $X^1$ and $X^2$ are each independently O or not present, $Y^1$ and $Y^2$ are selected from the compounds listed supra.

Then, after an acetyl functionalized PTFE polymer is formed, it can be diazeniumdiolated. At least one of the up to six hydrogen on the acetyl α-carbon (labeled $B^1$-$B^6$) is diazeniumdiolated.

Formula 2

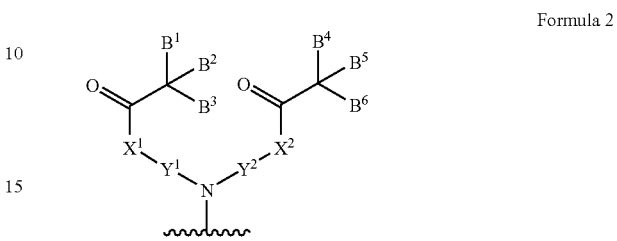

Diazeniumdiolation can be accomplished by either a wet or dry means. For a wet means, the acetyl functionalized PTFE polymer, whether alone or associated with an implantable medical device, is immersed within an appropriate solvent and subjected to NO gas which is bubbled through the solution. After a predetermined amount of time, the NO gas is suspended. This exposure to NO forms a NO-donating PTFE polymer cable of controlled release of NO in situ.

In contrast, for a dry means, the acetyl functionalized PTFE polymer, whether alone or associated with an implantable medical; device, is subjected to NO gas which is filled into an evacuated chamber and allowed to sit for a given period of time. After a predetermined amount of time, the NO gas removed from the chamber. This exposure to NO gas in a dry state forms a NO-donating PTFE polymer cable of controlled release of NO in situ, much the same as the wet process described supra.

The PTFE polymer may be converted to a NO-donating PTFE polymer before or after being associated with an implantable medical device. For example, the PTFE polymer can be coated onto a medical device and then converted to a NO-donating PTFE polymer. On the other hand, cylindrical sheets of PTFE polymer can be converted to a NO-donating PTFE polymer and then sown onto metal scaffolding forming a stent graft, or the cylindrical sheets of PTFE polymer can be sewn onto the scaffolding and then converted to a NO-donating PTFE polymer. The point of conversion is taken on a case by case basis and one skilled in the art will know which method will work best for a given medical device.

The following Examples are intended to illustrate non-limiting processes for forming NO-donating PTFE polymers and associated implantable medical devices according to the present description. One non-limiting example of a suitable metallic stent is the Medtronic/AVE S670™ 316L stainless steel coronary stent.

Example 1

Scheme 1

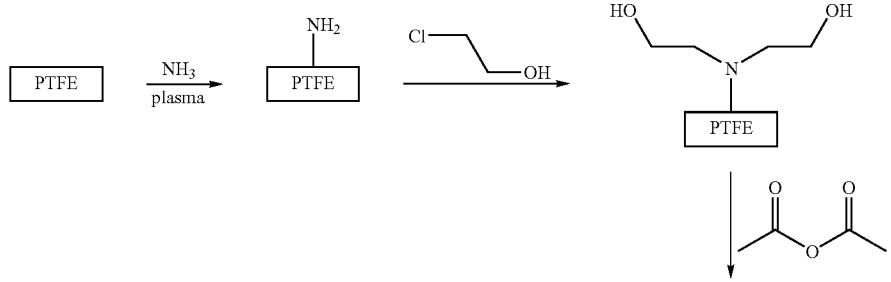

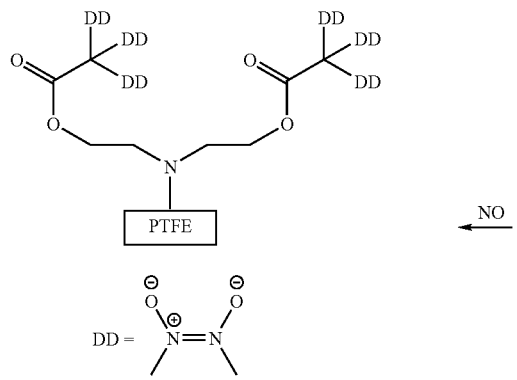

A sheet of 5 in×5 in PTFE polymer is placed in a plasma reaction chamber. The process is outlined in Scheme 1. The sheet of PTFE polymer is subjected to 2 min of ammonia plasma with 20 W of RF power, thereby enriching the PTFE surface with amino functional groups. The amino function groups are reacted with 2-chloroethanol, creating hydroxyl functionalized PTFE polymers. The hydroxyl functionalized PTFE polymers are then reacted with acetic anhydride thereby converting the exposed hydroxyl groups to fictionalized acetyl groups. The PTFE polymer, now with acetyl functionalized groups, are subjected to NO gas at 80 psi for 24 hr. After 24 hr, the sheet of PTFE polymer is removed can now donate and controllably release NO in situ.

Example 2

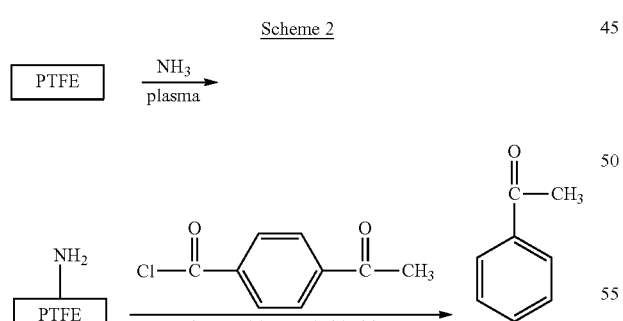

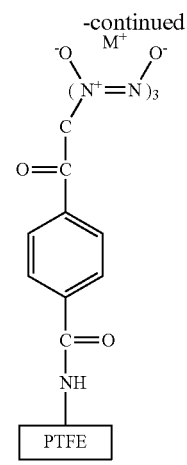

A sheet of 5 in×5 in PTFE polymer is placed in a plasma reaction chamber. The process is outlined in Scheme 2. The sheet of PTFE polymer is subjected to 2 min of ammonia plasma with 20 W of RF power, thereby enriching the PTFE surface with amino functional groups. The amino function groups are reacted with excess 4-acetyl benzoyl chloride with a base such as triethylamine for 4 hours. The PTFE polymer, now with acetyl functionalized groups, are subjected to NO gas at 80 psi for 24 hr. After 24 hr, the sheet of PTFE polymer is removed can now donate and controllably release NO in situ.

Example 3

NO-Donating PTFE Stent Graft

Cylindrical sheets of PTFE are subjected to the methods of Example 1 or 2 to form cylindrical sheets of NO-donating PTFE polymer. The cylindrical sheets are then attached to support scaffolding by sewing to form a NO-donating PTFE stent graft. In an alternate method, the cylindrical sheets of PTFE polymer are attached to support scaffolding by sewing and then subjected to the methods of Examples 1 or 2 to form a NO-donating PTFE stent graft. In one embodiment, the support scaffolding is the NO-donating PTFE polymer stent, and the scaffolding and the graft material can donate and controllably release NO.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

What is claimed is:

1. An implantable medical device comprising a nitric oxide-donating polytetrafluoroethylene polymer having a polymeric surface comprising the structure:

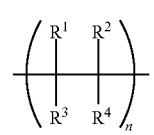

(Formula 1)

wherein n is an integer between 1 and 25,000 and wherein each of $R^1$, $R^2$, $R^3$, and $R^4$ is independently fluorine or a tertiary amine having the structure:

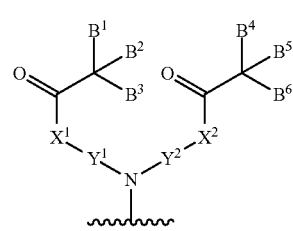

(Formula 2)

wherein $X^1$ and $X^2$ are each independently O or not present, $Y^1$ and $Y^2$ are each independently selected from $C_1$ to $C_{10}$ alkyl, $C_1$ to $C_{10}$ alkenyl, $C_1$ to $C_{10}$ alkynyl, $C_3$ to $C_8$ cyclic alkyl, or any combination thereof, and each of $B^1$, $B^2$, $B^3$, $B^4$, $B^5$, and $B^6$ is independently hydrogen or a diazeniumdiolate (DD) group, with the proviso that at least one of $B^1$, $B^2$, $B^3$, $B^4$, $B^5$, and $B^6$ is a DD group; wherein at least one of $R^1$, $R^2$, $R^3$, and $R^4$ is a tertiary amine of the structure of Formula 2.

2. The implantable medical device of claim 1 wherein said implantable medical device is selected from the group consisting of stents, catheters, micro-particles, probes, vascular grafts, and combinations thereof.

3. The implantable medical device of claim 1 wherein said polymer comprises one or more bioactive agents other than the nitric oxide.

4. The implantable medical device of claim 3 wherein said at least one bioactive agent is selected from the group consisting of anti-proliferatives, estrogens, chaperone inhibitors, protease inhibitors, protein-tyrosine kinase inhibitors, leptomycin B, peroxisome proliferator-activated receptor gamma ligands (PPARγ), hypothemycin, bisphosphonates, epidermal growth factor inhibitors, antibodies, proteasome inhibitors, antibiotics, anti-inflammatories, anti-sense nucleotides and transforming nucleic acids, cytostatic compounds, toxic compounds, chemotherapeutic agents, analgesics, antibiotics, protease inhibitors, statins, nucleic acids, polypeptides, growth factors and delivery vectors, and liposomes.

5. The implantable medical device of claim 1 wherein $Y^1$ and $Y^2$ are each —$CH_2$—.

6. The implantable medical device of claim 1 wherein said nitric oxide-donating polytetrafluoroethylene polymer provides controlled release of nitric oxide once implanted at or within the target site.

7. The implantable medical device of claim 1 wherein said nitric oxide-donating polytetrafluoroethylene polymer forms a coating layer on at least a portion of a surface of the implantable medical device.

8. The implantable medical device of claim 7 further comprising a parlyene primer layer between the implantable medical device surface and the nitric oxide-donating polytetrafluoroethylene polymer coating layer.

9. The implantable medical device of claim 8 further comprising a cap coat disposed over the nitric oxide-donating polytetrafluoroethylene polymer coating layer.

10. A nitric oxide-donating vascular stent comprising:
a stent; and
a polymer coating disposed upon said stent wherein said polymer is a nitric oxide-donating polytetrafluoroethylene polymer having a polymeric surface comprising the structure:

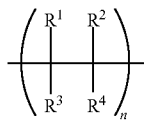

(Formula 1)

wherein n is an integer between 1 and 25,000 and wherein each of $R^1$, $R^2$, $R^3$, and $R^4$ is independently fluorine or a tertiary amine having the structure:

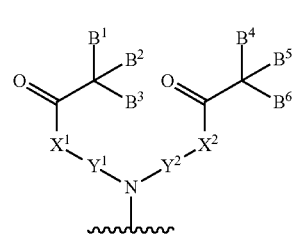

(Formula 2)

wherein $X^1$ and $X^2$ are each independently O or not present, $Y^1$ and $Y^2$ are each independently selected from $C_1$ to $C_{10}$ alkyl, $C_1$ to $C_{10}$ alkenyl, $C_1$ to $C_{10}$ alkynyl, $C_3$ to $C_8$ cyclic alkyl, or any combination thereof, and each of $B^1$, $B^2$, $B^3$, $B^4$, $B^5$, and $B^6$ is independently hydrogen or a diazeniumdiolate (DD) group, with the proviso that at least one of $B^1$, $B^2$, $B^3$, $B^4$, $B^5$, and $B^6$ is a DD group; wherein at least one of $R^1$, $R^2$, $R^3$, and $R^4$ is a tertiary amine of the structure of Formula 2.

11. The vascular stent of claim 10 wherein said polymer comprises one or more bioactive agents other than the nitric oxide.

12. The vascular stent of claim 11 wherein said at least one bioactive agent is selected from the group consisting of anti-proliferatives, estrogens, chaperone inhibitors, protease inhibitors, protein-tyrosine kinase inhibitors, leptomycin B, peroxisome proliferator-activated receptor gamma ligands (PPARγ), hypothemycin, bisphosphonates, epidermal growth factor inhibitors, antibodies, proteasome inhibitors, antibiotics, anti-inflammatories, anti-sense nucleotides and transforming nucleic acids, cytostatic compounds, toxic compounds, chemotherapeutic agents, analgesics, antibiotics, protease inhibitors, statins, nucleic acids, polypeptides, growth factors and delivery vectors, and liposomes.

13. The vascular stent of claim 10 wherein said nitric oxide-donating polytetrafluoroethylene polymer provides controlled release of nitric oxide once implanted at or within the target site.

14. The vascular stent of claim 10 wherein $Y^1$ and $Y^2$ are each —$CH_2$—.

15. The vascular stent of claim 10 wherein said nitric oxide-donating polytetrafluoroethylene polymer forms a coating layer on at least a portion of a surface of the vascular stent.

* * * * *